United States Patent [19]

Lübbers

[11] 4,273,442

[45] Jun. 16, 1981

[54] SPECTRAL PHOTOMETER FOR MEDICAL APPLICATIONS

[75] Inventor: Dietrich W. Lübbers, Dortmund, Fed. Rep. of Germany

[73] Assignee: Max Planck Gesellschaft zur Förderung der Wissenschaften e.V., Göttingen, Fed. Rep. of Germany

[21] Appl. No.: 27,850

[22] Filed: Apr. 6, 1979

[30] Foreign Application Priority Data

Apr. 7, 1978 [DE] Fed. Rep. of Germany ....... 2815074

[51] Int. Cl.³ .................... G01J 3/34; G01N 33/48
[52] U.S. Cl. ................................ 356/326; 356/41; 356/303; 356/308
[58] Field of Search ............. 356/303, 308, 326, 328, 356/40, 41

[56] References Cited

U.S. PATENT DOCUMENTS

| | | | |
|---|---|---|---|
| 2,480,636 | 8/1949 | Dieke | 356/308 |
| 2,630,736 | 3/1953 | Beitz | 356/308 |
| 3,012,467 | 12/1961 | Rosenthal | 356/308 |
| 3,829,218 | 8/1974 | Alyanak | 356/326 |
| 4,146,332 | 3/1979 | Moore | 356/308 |

Primary Examiner—Vincent P. McGraw
Attorney, Agent, or Firm—Michael J. Striker

[57] ABSTRACT

A spectral photometer emits light towards an object of interest, receives the light reflected back from the object of interest, and includes a timer or synchronizer operative for causing the spectral photometer to produce an output signal whose successive values correspond to the intensity of the spectrum derived from the object of interest at successive wavelengths. The spectral photometer output signal is applied to an oscilloscope for display of the thusly generated spectrum. The oscilloscope screen is provided with interpretation marks at characteristic points of the displayed spectrum, either by providing such marks on a transparent plate mounted in front of the screen, or by applying to the oscilloscope signals causing the scope itself to generate these marks. These marks may be curves shaped and located to be intersected by both maxima of an oxygenated-hemoglobin spectrum irrespective of the degree of oxygenation. The distance between the interpretation marks automatically provided can be automatically measured to generate an indication of their wavelength difference. The interpretation marks can also be in the form of a complete reference or comparison spectrum, selected out from a storage storing a plurality of such reference spectra, and applied as a signal to the scope to effect superimposed display of both the spectrum derived from the spectral photometer and the selected reference spectrum.

4 Claims, 5 Drawing Figures

SPECTRAL PHOTOMETER FOR MEDICAL APPLICATIONS

BACKGROUND OF THE INVENTION

The present invention concerns spectral photometers, of the type typically comprising a source of illumination and a monochromator, and at least one measuring-beam path as well as a light-metering unit provided with an indicator, with the measuring-beam path and the light path from the source of illumination being defined by a single, common light-conductive structure, one part of the light-conductive structure transmitting light to the object of interest and the other part of the light-conductive structure transmitting the reflected light to the monochromator, with the spectrum of the monochromator completely projected onto the light-metering unit, the latter advantageously designed as an array of photocells each photocell of which generates a signal pertaining to a different respective portion of such spectrum, and with a synchronizer or timer being used to transmit the output signals of successive photocells of the photocell array to the signal input of an oscilloscope or other such display device, e.g., as disclosed in Federal Republic of Germany patent application Ser. No. P 27 26 606.4 but merely by way of example.

Systems of this type are in general employed in medical applications where an overview of spectral information is required.

SUMMARY OF THE INVENTION

It is a general object of the invention to facilitate the quickest possible development of a quantitative interpretation of a thusly generated spectrum.

In accordance with the present invention, this is achieved by providing marks on the oscilloscope screen at characteristic points of the spectrum displayed.

The present invention, although not exclusively, is particularly concerned with the display of hemoglobin spectra derived from use of a spectral photometer of the type referred to above upon the surface of body tissue. In that context, the concept of the present invention is particularly applicable, because the marks can be located on the screen at those locations, or otherwise correlated with, the invariants of the displayed hemoglobin spectrum. For example, the spacing between the maxima of an oxygenated-hemoglobin spectrum is dependent upon the degree of oxygenation but independent of intensity and other additive interference components, i.e., independent from the white component of the light-metering unit of the spectral photometer.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

DESCRIPTION OF THE PREFERRED EMBODIMENTS

Figure 1:
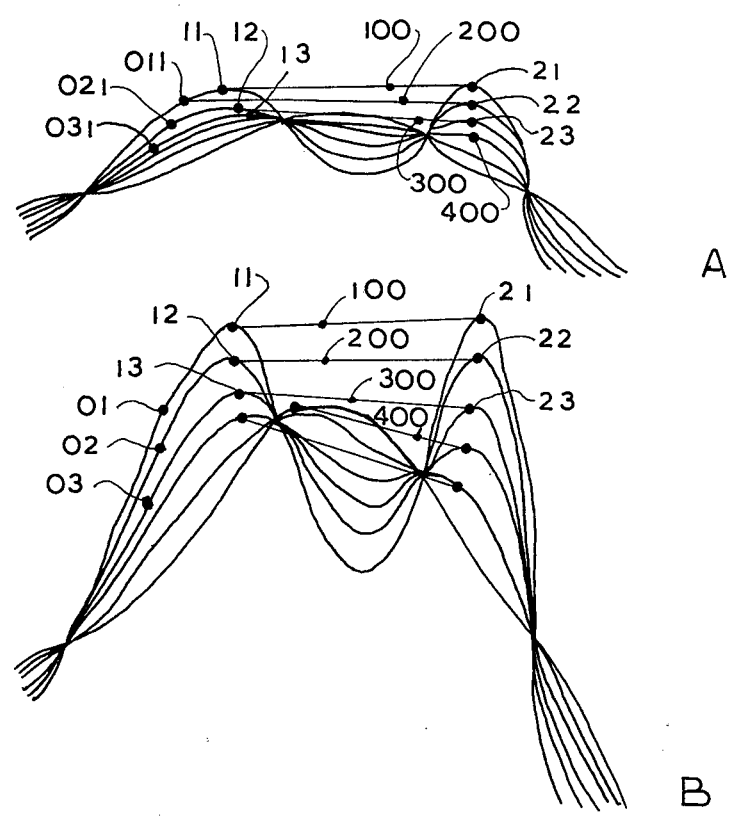
FIGS. 1a and 1b depict two families of oxygenated-hemoglobin spectra corresponding to different degrees of hemoglobin oxygenation.

Some of the concepts of the present invention will first be elucidated with respect to FIGS. 1a and 1b. FIG. 1b depicts a family of oxygenated-hemoglobin spectra 01, 02, 03, . . . , corresponding to different degrees of hemoglobin oxygenation. Numeral 100 denotes the distance between the maxima of the spectrum for 100% oxygenated hemoglobin; 200 the intermaxima distance of the spectrum for 80% oxygenated hemoglobin; 300 for 60% oxygenation; and 400 for 40% oxygenation; all curves illustrated being derived using pure hemoglobin contained in a curvette. In contrast, in the similar family of oxygenated-hemoglobin spectra shown in FIG. 1a, derived from use of a spectral photometer upon the surface of blood-perfused tissue, the oxygenated-hemoglobin spectra are strongly influenced by the strong white component of the light metered by the spectral photometer, and accordingly have intensities not corresponding to those shown in FIG. 1b. However, the intermaxima spacings 100, 200, . . . , for different degrees of hemoglobin oxygenation are the same as in FIG. 1a, the intermaxima spacing for a given degree of hemoglobin oxygenation being an invariant.

Figure 2:
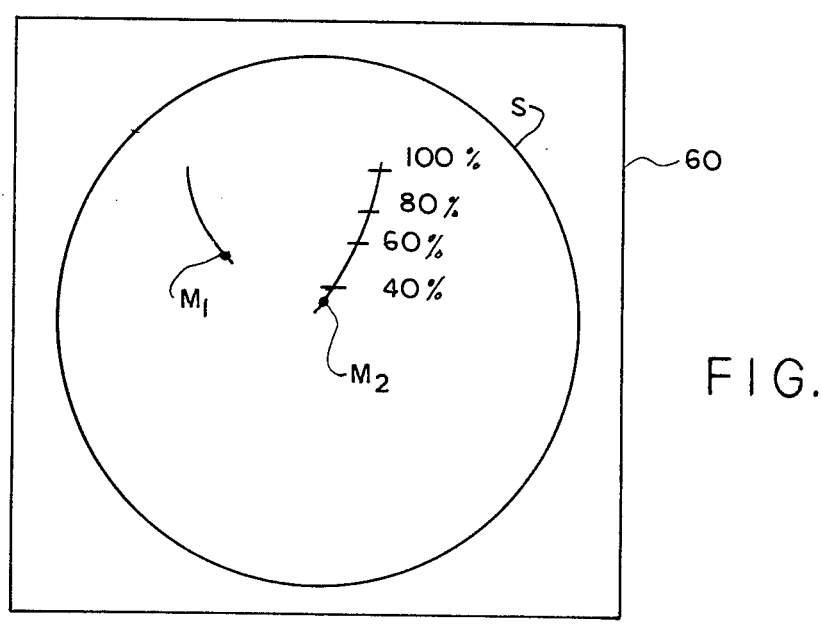
FIG. 2 depicts a transparent plate provided with interpretation marks in accordance with the invention, mounted on the display screen of an oscilloscope used with a spectral photometer.

In accordance with one advantageous concept of the invention, depicted in FIG. 2, the oscilloscope screen 60 is provided with a transparent plate S on which are provided marks which are to coincide with characteristic points of the displayed oxygenated-hemoglobin spectrum, namely with the two maxima 11 and 21, or 12 and 22, or 13 and 23, . . . , corresponding to differing degrees of oxygenation. In this way, the degree of hemoglobin oxygenation can be read off the displayed curve very directly and immediately.

Advantageously, the transparent plate S is removably provided on the oscilloscope screen 60, and is provided with two curves M1, M2 so shaped as to be intersected by both maxima of successive oxygenated-hemoglobin spectra of successively different degrees of oxygenation. When a particular oxygenated-hemoglobin spectra is being displayed, the technician manipulates the x- and y-displacement dials of the oscilloscope until both maxima of the displayed curve are intersecting the two curves M1, M2. Advantageously, one of the two curves M1, M2 is provided with legible calibrations directly indicating the degree of hemoglobin oxygenation involved.

In accordance with a further concept of the invention, discussed further below, the marks to be provided on the screen at characteristic points of the spectrum can be generated by a micropressor operating in synchronism with the spectral photometer and electronically displayed on the oscilloscope screen superimposed upon the displayed spectrum. Using that technique, the means generating the interpretation marks can readily be designed to permit the technician to effect electronic shifting of the interpretation marks, to bring them into proper superposition upon the displayed spectrum, instead of vice versa.

In such case, the interpretation marks can for example be developed by control of the unblanking of the oscilloscope's electron beam. Because the sweep time of the scanning beam can be synchronized with operation of the spectral photometer, the sweep time can be directly correlated with a wavelength interval or range, and accordingly by appropriately selecting the start and end points of the scanning beam's sweep period, i.e., intermediate beam unblanking and reblanking, a corresponding wavelength interval or range can be directly established on the oscilloscope screen. The marks thusly established by control of beam unblanking can readily be electronically shifted in each of two mutually perpendicular directions, so that these can readily be brought into register with the maxima of a displayed spectrum. The sweep period established in order to bring such registry about then corresponds per se to the wavelength interval intermediate the spectrum's maxima and can be applied to a digital indicator for direct digital display of the inermaxima wavelength difference or for direct digital display of the degree of hemoglobin oxygenation per se. Furthermore, by generating a signal corresponding to the slope of the displayed spectrum, it becomes simple to automatically identify the spectrum's maxima and to automatically measure the intermaxima wavelength interval of the spectrum. In this way, the degree of oxygenation of the body tissue of interest can be indicated fully automatically with very little or no intervention by the technician.

Alternatively, for example in the case of spectra not exhibiting such invariants, but also in the case of spectra which do exhibit such invariants, the interpretation marks can be more complex and in the form of complete reference or comparison spectra electronically generated and displayed on the oscillscope screen in superposition upon the spectrum generated by the spectral photometer. Such comparison spectra can be stored and read out from a storage.

Figure 3:
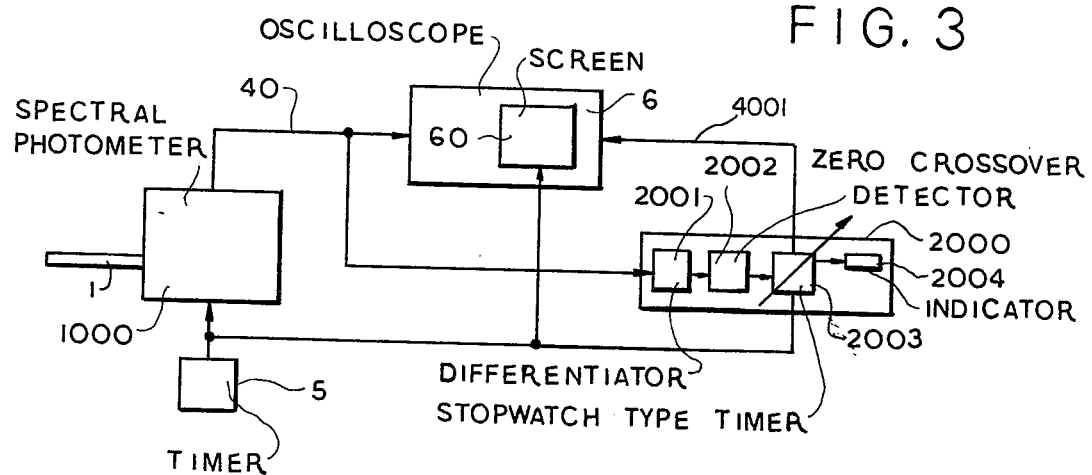
FIG. 3 depicts an arrangement for automatically reading out the degree of hemoglobin oxygenation.

In FIG. 3, numeral 1000 denotes a spectral photometer of the type provided with a source of illumination and a monochromator, and having means defining a measuring-beam path and a source-illumination beam path, here in the form of a shared light-conductive structure 1 a part of which transmits light to the (non-illustrated) body tissue of interest and another part of which receives the light reflected from the tissue of interest and transmits it back into the spectral photometer to the internal light-metering unit thereof. The spectral photometer 1000 produces on its output line 40 a signal whose value at successive instants corresponds to the intensity of the photometrically generated spectrum at successive different wavelengths of the spectrum, for application to the signal input of an oscilloscope or other such display device 6 having a display screen 60. A synchronizer or timer 5 determines the progression of wavelengths of the spectrum whose intensity values are to be successively read out on output line 40, i.e., for sequential generation of the spectrum display. The timer or synchronizer 5 is furthermore connected to the sweep input of the oscilloscope 6 for synchronized control of its horizontal sweep. The spectral photometer 1000 can be of the type in which the wavelength of its internal monochromator is progressively varied under the control of synchronizer or timer 5 and using, essentially, a single internal light-sensitive element. Alternatively, the spectral photometer 1000 can be of the type in which an array of photocells is provided, with the measurement beam received back from the tissue of interest projected onto the photocell array in such a manner that the electrical signal produced by each photocell of the array corresponds to the intensity of the spectrum at a different respective wavelength value, with the synchronizer or timer 5 being used, in that case, to effect sequential read-out of the signals produced by successive photocells of the photocell array.

The signal produced on output line 40 is additionally applied to the input of a simple microprocessor 2000, and in particular applied to the input of a differentiator stage 2001 therein for development of a signal indicating the instantaneous slope of the generated spectrum being displayed. The output signal of differentiator stage 2001 is applied to the input of a pulse generator 2002 which is operative for producing an output pulse in response to a zero-crossover value of the slope-indicating signal at the output of stage 2001 when the zero-crossover value occurs subsequent to a positive slope indication, i.e., this serving to indicate the presence of a maximum of the displayed spectrum. This output pulse initiates operation of a stopwatch-type timer 2003 provided with an indicator 2004, and furthermore results in the appearance of an unblanking signal on beam-blanking control line 4001 of the oscilloscope 6. This results in the establishment of an interpretation mark coincident with the first maximum of the spectrum being sequentially generated. As soon as an output pulse is produced by stage 2002 in response to the spectrum's next maximum, a reblanking signal appears on line 4001, this serving to constitute a second interpretation mark coincident with the second maximum of the spectrum, and the stopwatch-type timer 2003 stops, the elapsed-time indication developed on indicator 2004 now being held. Instead of merely unblanking and reblanking the oscilloscope's electron beam at the first and second maxima, respectively, it is alternatively very advantageous, in order that no spectral information generated fail to appear on the screen, to briefly boost the intensity of the scope's scanning beam concurrently with the reaching of the first and second maxima of the spectrum, in order to produce on the screen bright and easily seen spots at the first and second maxima. The elapsed-time indication now present on indicator 2004 is directly correlatable with the wavelength difference between the two maxima, and therefore with the degree of hemoglobin oxygenation. If desired, the microprocessor 2000 can be calibrated directly in units of wavelength difference or directly in units of hemoglobin oxygenation.

Alternatively, the microprocessor 2000 can be disconnected from the output signal line 40 of the spectral photometer 1000, with the location of the first and second interpretation marks being fixed but adjustable by the technician, i.e., by the technician manually preselecting the points at which the timer 2003, in response to the signal received from the synchronizer 5, produces the first and second interpretation marks.

Figure 4:
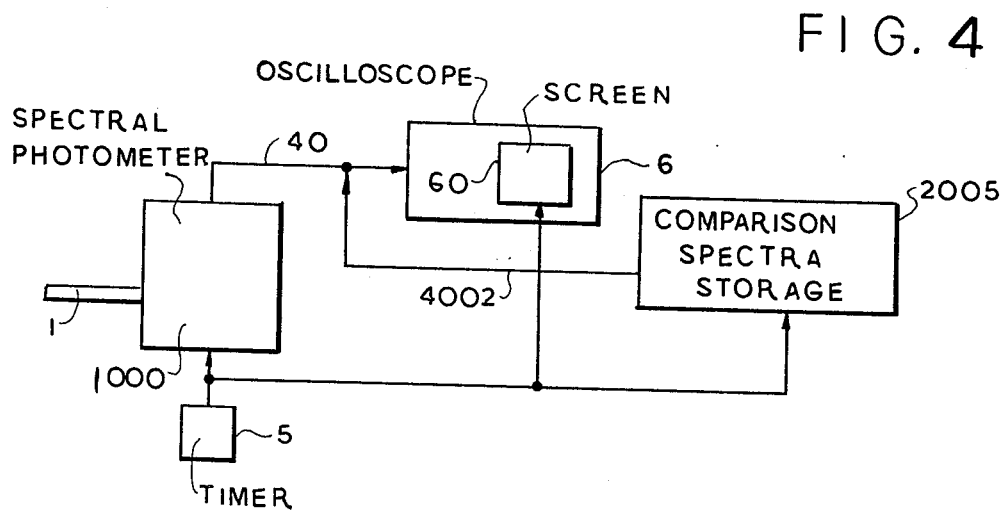
FIG. 4 depicts an arrangement in which the spectrum displayed on the oscilloscope screen is to have superimposed thereon a complete reference or comparison spectrum furnished from a storage.

FIG. 4 schematically depicts an alternative embodiment, in which components corresponding to those of FIG. 3 are indicated by the same reference numerals as there. Again, the spectral photometer 1000 can be of either of the two types mentioned earlier. In this embodiment, instead of simple interpretation marks, complex interpretation marks in the form of a complete reference or comparison spectrum are superimposed upon the spectrum generated by spectral photometer 1000 and displayed on the oscilloscope screen, i.e., the two spectra are displayed simultaneously, and the oscilloscope employed should be of the type capable of simultaneously displaying two curves. The reference or comparison spectra to be displayed are stored in an electronic storage 2005 whose read-out is performed in synchronism with the operation of the synchronizer or timer 5 of spectral photometer 1000. The signal read out from storage 2005 is applied to the oscilloscope 6 via a line 4002. During persisting or repeated display of the spectrum generated by spectral photometer 1000, the technician commands read-out of different ones of the various spectra stored in storage 2005, each stored spectrum being associated with a known value of the quantity of interest, e.g., degree of hemoglobin oxygenation. More than one spectrum for each given value of the quantity of interest can be included, to take into account the differing shapes of the spectrum which may be produced by spectral photometer 1000 in dependence upon varying levels of intensity, i.e., as explained with regard to FIGS. 1*a* and 1*b*. When the technician has found the one reference or comparison spectrum which comes into the closest register with the displayed spectrum generated by spectral photometer 1000, the technician takes note of the value of the quantity of interest associated with that one of the stored reference spectra. The advantage of this alternative embodiment is that it is particularly useful in the case of displayed spectra which do not exhibit the invariant characteristics of, for example, an oxygenated-hemoglobin spectrum such as discussed above.

It will be understood that each of the elements described above, or two or more together, may also find a useful application in other types of systems and spectrum-evaluation procedures, differing from the types described above.

While the invention has been illustrated and described as embodied in methods and systems used for determining the degree of hemoglobin oxygenation from the oxygenated-hemoglobin spectrum generated by a spectral photometer, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A spectral photometer for medical applications, comprising:
   a spectral photometer stage providing a spectral display signal from a sample under investigation;
   a display unit responding to the spectral display signal and visually displaying it to a user;
   a maximum detector responding to the spectral display signal and detecting successive maxima therein; and
   an intermaximum calculator cooperating with the maximum detector and cooperating with the display to visually display distance between successive maxima in the spectral display signal.

2. The spectral photometer defined by claim 1, wherein the display unit is an oscilloscope.

3. The spectral photometer defined by claim 2, wherein the intermaximum calculator is a timer timing sweep time required for a display of horizontal distance between two successive maxima in the spectral display signal.

4. The spectral photometer defined by claim 2, wherein the maximum detector includes a differentiator responsive to slope of the spectral display signal and further includes a zero crossover detector responsive to the differentiator and indicating when a positive slope changes to a negative slope by passing through zero.

* * * * *